(12) United States Patent
Herlinger et al.

(10) Patent No.: US 6,909,010 B2
(45) Date of Patent: Jun. 21, 2005

(54) FACILE SYNTHESIS OF SYMMETRIC ESTERS OF ALKYLENEBISPHOSPHONIC ACIDS

(75) Inventors: Albert W. Herlinger, Glenview, IL (US); Dominique C. Stepinski, Chicago, IL (US)

(73) Assignee: Loyola University of Chicago, Chicago, IL (US)

( * ) Notice: Subject to any disclaimer, the term of this patent is extended or adjusted under 35 U.S.C. 154(b) by 74 days.

(21) Appl. No.: 10/116,952

(22) Filed: Apr. 5, 2002

(65) Prior Publication Data

US 2003/0060648 A1 Mar. 27, 2003

Related U.S. Application Data

(60) Provisional application No. 60/282,952, filed on Apr. 11, 2001.

(51) Int. Cl.[7] ............................. C07F 9/02; C07F 9/28
(52) U.S. Cl. ........................... 558/70; 558/87; 558/89; 558/90; 558/92; 562/20; 562/21; 562/22; 548/250; 548/255
(58) Field of Search ............................. 558/70, 87, 89, 558/90, 92; 562/20, 22; 548/250, 255

(56) References Cited

U.S. PATENT DOCUMENTS

| | | | | |
|---|---|---|---|---|
| 3,156,739 A | * | 11/1964 | Klink et al. ................. | 585/436 |
| 4,548,790 A | | 10/1985 | Horwitz et al. | |
| 4,574,072 A | | 3/1986 | Horwitz et al. | |
| 4,835,107 A | | 5/1989 | Horwitz et al. | |
| 5,651,883 A | | 7/1997 | Horwitz et al. | |
| 5,851,401 A | | 12/1998 | Horwitz et al. | |

OTHER PUBLICATIONS

Raskina et al (1968): STN CAS International CAPLUS database, Columbus, Ohio, document No. 69:86266.*
Horwitz, et al., "DIPEX: A New Extraction Chromatographic Material for the Separation and Preconcentration of Actinides from Aqueous Solution," *Reactive and Functional Polymers* 33: 25–36 (1997).
Chiarizia, et al., "Metal Extraction by Alkyl Substituted Diphosphonic Acids, Part 1. P, P'–DI (2–Ethylhexyl) Methanediphosphonic Acid," *Solvent Extr. Ion Exchange* 14: 773–792 (1996).
J. March, *Advanced Organic Chemistry: Reactions, Mechanisms and Structure*, 4th Edition, John Wiley & Sons, New York (1992) pp. 348–352.
Stepinski, et al., "Facile high yielding synthesis of symmetric esters of methylenebisphosphonic acid," *Tetrahedron* 52: 8637–8645 (2001).
Griffith–Dzielawa, et al., "Synthesis and Characterization of DI[3–(Trimethylsilyl)–1–Propylene] Alkylenediphosphonic Acids," *Synth. Commun.*, 30: 2121–2132 (2000).
Zhao, et al., "Tetrazole Catalyzed Synthesis of Phosphonate Esters," *Tetrahedron* 49:(2) 363–368 (1993).

McKenna, et al., "Functional Selectivity in Phosphonate Ester Dealkylation with Bromotrimethylsilane," *J. Chem. Soc. Chem. Commun.*, 739 (1979).
McKenna, et al., "The Facile Dealkylation of Phosphonic Acid Dialkyl Esters by Bromotrimethylsilane ," *Tetrahedron Letter* 2: 155–158 (1977).
Lesiak, et al., "2–(4–Nitrophenyl)ethyl Methylenebis(Phosphonate): A Versatile Reagent for the Synthesis of Nucleoside 5'–Methylenebis(Phosphonate)s," *J. Org. Chem.* 63: 1906–1909 (1998).
Vepsalainen, et al., "An Improved Synthetic Method and the First Crystal Structures for (Dihalomethylene)bisphosphonate Partial Esters," *Tetrahedron* 51: 6805–6818 (1995).
Vepsalainen, et al., "Bisphosphonic Compounds VIII. A Facile and Selective One–Pot Synthesis of P,P–Dialkyl (Dichloromethylene)bisphosphonate Partial Esters," *Tetrahedron Lett.* 37: 3533–3536 (1996).
Vepsalainen, et al., "Bisphosphonic Compounds V. Selective Preparation of (Dichloromethylene)bisphosphonate Partial Esters," *Tetrahedron Lett.* 34: 4551–4554 (1993).
Morita, et al., " Dealkylation Reaction of Acetals, Phosphonate, and Phosphate Esters with Chlorotrimethylsilane/ Metal Halide Reagant in Acetonitrile, and Its Application to the Synthesis of Phosphonic Acids and Vinyl Phosphates," *Bull. Chem. Soc., Japan,* 54: 267–273 (1981).
Petrow, et al., "Cyclohexyl Alkylenediphosphonates and Some of Their Properties," *J. Gen. Chem. USSR* 39: 809–811 (1969).
Krawczyk, "A Convenient Route for Monodealkylation of Diethyl Phosphonates," *Synthetic Communications* 27: 3151–3161 (1977).
Lang, et al., "Synthese von Phenoxygruppenhaltige Derivate der Methandiphosphonsaure," *Z. Anorg. Allg. Chem.*, 56: 187–196 (1986).

(Continued)

*Primary Examiner*—Golam M M Shameem
(74) *Attorney, Agent, or Firm*—Welsh & Katz, Ltd.

(57) ABSTRACT

A facile synthesis of symmetric esters of $C_1$–$C_{10}$ alkylenebisphopsphonic acids is disclosed in which a $C_1$–$C_{10}$ alkylenebis(phosphonic dichloride) is reacted with an alcohol in the presence of a catalytic amount of 1H-tetrazole and a base in an aprotic solvent to form a first reaction mixture. The first reaction mixture is maintained for a time period sufficient to form a $C_1$–$C_{10}$ alkylenebis(chloro ester phosphonate) that is reacted under basic conditions with an excess of a hydroxylated compound to form a second reaction mixture that is itself maintained for a time period sufficient to form a $C_1$–$C_{10}$ alkylenebis(ester phosphonate) partial ester, homoleptic tetraester or mixed tetraester. The material so formed can be recovered or used as is.

49 Claims, No Drawings

OTHER PUBLICATIONS

Sober, et al., Eds., "Physical and Chemical Data—Ionization Constants of Acids and Bases (Continued) and Nitrogen Compounds (Continued)," *CRC Handbook of Biochemistry*, Second Edition, The Chemical Rubber Company, Cleveland, OH (1970) pp. 209–220.

McKenna, et al., "Fluorination of Methanediphosphonate Esters by Perchloryl Fluoride. Synthesis of Fluoromethanediphosphonic Acid and Difluoromethanediphosphonic Acid," *J. Org. Chem.*, 46: 4573–4576 (1981).

Morita, et al., "A Convenient Dealkylation of Dialkyl Phosphonates by Chlorotrimethylsilane in the Presence of Sodium Iodide," *Tetrahedron Letters* 28: 2523–2526 (1978).

CRC Handbook of Chemistry and Physics, 3rd Electronic Edition, *CRC Press LLC* (2001).

\* cited by examiner

FACILE SYNTHESIS OF SYMMETRIC ESTERS OF ALKYLENEBISPHOSPHONIC ACIDS

CROSS-REFERENCE TO RELATED APPLICATION

This a continuation-in-part of co-pending application Ser. No. 60/282,952, filed Apr. 11, 2001, whose disclosures are incorporated herein by reference.

BACKGROUND ART

The recovery and isolation of radionuclides from environmental and bioassay samples is complicated by the presence of silica, aluminum and iron (III) as well as other frequently present ions such as titanium, bismuth and phosphate. The isolation of the actinides, lanthanides and radium from such samples in the past has involved time-consuming, expensive and sometimes hazardous procedures.

A number of previously described procedures for the determination of the actinide plutonium (Pu) in urine, for example, involved preconcentration of small amounts of Pu from the vast excess of matrix substances present in urine samples by precipitation reactions, adsorption on glass fiber, extraction, extraction chromatography or ion exchange. Of these, precipitation reactions appear to provide the most satisfactory results. However, such methods are complex, time consuming and relatively expensive.

U.S. Pat. No. 4,548,790 dated Oct. 22, 1985 describes a group of neutral bifunctional organophosphorus compounds broadly described as alkyl(phenyl)-N,N-dialkyl-carbamoylmethylphosphine oxides (hereinafter referred to as CMPO) that are useful for the recovery of actinide and lanthanide values from acidic solutions containing these and other metal values. The combination of the CMPO extractants with a phase modifier such as tri-n-butyl phosphate in a normal paraffin hydrocarbon diluent is described in U.S. Pat. No. 4,574,072. U.S. Pat. No. 4,835,107 describes passing samples in a mineral acid solution through a separation column of an alkyl(phenyl)-N,N-dialkylcarbamoyl-methylphosphine oxide dissolved in tri-n-butyl phosphate on an inert support to selectively recover actinides.

U.S. Pat. Nos. 5,651,883 and 5,851,401, each to Horwitz et al., and Horwitz et al., *Reactive and Functional Polymers*, 33:25–36 (1997) teach the use of a diesterified methylenebi-sphosphonic acid extractant adsorbed on a solid support for the separation of trivalent, tetravalent and hexavalent actinide and lanthanide cations, as well as radium cations from aqueous solutions. The particularly preferred extractant of those patents is P,P'-bis(2-ethylhexyl) methylenebisphosphonic acid, that can also be named methylenebis(2-ethylhexyl hydrogen phosphonate), or $H_2DEH[MBP]$. Methylenebis-(2-ethylhexyl hydrogen phosphonate) extractant is available commercially under the name Dipex® from Eichrom Technologies, Inc., of Darien, Ill.

Although particularly effective for removing those polyvalent cations, those bis-ester phosphonates are difficult and costly to prepare. For example, the synthesis of the preferred extractant, methylenebis(2-ethylhexyl hydrogen phosphonate), typically involves carbodiimide-promoted coupling of methylenebis(phosphonic acid) with 2-ethylhexanol in boiling tetrahydrofuran (THF) for several days, followed by extractions from ammonia solution and then acid solution. Chiarizia et al., *Solvent Extr. Ion Exch.*, 14:773–792 (1996). This reaction is slow, and separation of the desired product from the other ester products requires a series of difficult extractions. In turn, these extractions generate large volumes of waste. This purification process makes large-scale synthesis of methylenebis(2-ethylhexyl hydrogen phosphonate) [Dipex®] laborious and costly to prepare.

It would therefore be advantageous if an easier and less costly, high yield synthesis could be provided. The disclosure below describes one such process.

BRIEF SUMMARY OF THE INVENTION

A first aspect of the invention contemplates the reaction of a $C_1$–$C_{10}$ alkylenebis(phosphonic acid dichloride) with two equivalents of an alcohol having a molecular weight of about 250 or less such as a preferred $C_4$–$C_{10}$ alcohol under mild, anhydrous, basic conditions in the presence of a catalytic amount of a cyclic aromatic amine, which is preferably an alpha-effect cyclic aromatic amine, to form a corresponding bisphosphonic ester acid chloride [or alkylenebis(chloro ester phosphonate)]. The resulting ester acid chloride is reacted under basic conditions with an excess of a hydroxylated compound, YOH, that can be water, the same or different alcohol having a molecular weight of about 250 or less or a primary $C_1$–$C_8$ alcohol to form the corresponding partial ester (diester) or tetraester (homoleptic or mixed tetraester), respectively. Where a mixed or homoleptic tetraester is formed, that compound is preferably hydrolyzed to form the corresponding partial ester. Where YOH is other than water, basic reaction conditions are preferably used.

In one more specific aspect of the invention, symmetric P,P'-diesters of $C_1$–$C_{10}$ alkylenebisphosphonic acid are prepared in high yield and high purity from the corresponding acid chloride using a facile two-step, one-pot process. The first step in the synthesis utilizes a cyclic aromatic amine, which is preferably an alpha-effect cyclic aromatic amine, to catalyze the regio-selective condensation of $C_1$–$C_{10}$ alkylenebis(phosphonic dichloride) with two equivalents of alcohol under mild, anhydrous, basic conditions to form a corresponding bisphosphonic ester acid chloride. In the second step, the partial ester is formed directly when the unreacted P—Cl groups are quenched with water.

Another more specific aspect of the invention contemplates preparation of symmetric $C_1$–$C_{10}$ alkylenebisphosphonic acid partial esters from the corresponding homoleptic $C_1$–$C_{10}$ alkylenebisphosphonates or the P,P'-mixed dimethyl $C_1$–$C_{10}$ alkylenebisphosphonate esters by selective deprotection of the corresponding tetraesters. These compounds can also be named as the $C_1$–$C_{10}$ alkylenebis(dialkyl or alkyl methyl phosphonate); i.e., $R_4$[MBP] and $R_2Me_2$[MBP] respectively.

These partial ester compounds are prepared by the cyclic aromatic amine-catalyzed esterification of $C_1$–$C_{10}$ alkylenebis(phosphonic dichloride) using a procedure similar to that described above for the synthesis of P,P'-dialkyl alkylenebisphosphonic acids, and wherein the cyclic aromatic amine is preferably an alpha-effect cyclic aromatic amine. In one modified procedure, excess methanol is used in the second step in place of water to quench the reaction. The alkylenebis(alkyl methyl phosphonate) thus formed is then preferably selectively cleaved to form the partial ester.

Alternatively, partial ester compounds are prepared by the cyclic aromatic amine-catalyzed esterification of $C_1$–$C_{10}$ alkylenebis(phosphonic dichloride) using an excess of the first alcohol (ROH) to form the homoleptic tetraester that is then preferably selectively cleaved to form the partial ester.

The mixed and homoleptic tetraesters are typically stable products that can be readily isolated and stored for later use as partial esters and are therefore contemplated end products.

DETAILED DESCRIPTION OF THE INVENTION

The present invention broadly contemplates the reaction of a $C_1$–$C_{10}$ alkylenebis(phosphonic acid dichloride) with an alcohol having a molecular weight of about 250 or less, which is preferably a $C_4$–$C_{10}$ alcohol, under mild, anhydrous, basic conditions to form a corresponding bisphosphonic ester acid chloride. The resulting ester acid chloride is reacted under basic conditions with an excess of a hydroxylated compound, YOH, that can be water, the same or different alcohol or a primary $C_1$–$C_8$ alcohol to form the corresponding partial ester, homoleptic tetraester, or mixed tetraester, respectively. A catalytic amount of a cyclic aromatic amine is also present in the reaction medium. Reaction with YOH is preferably carried out under basic conditions where YOH is not water. Where a mixed or homoleptic tetraester is formed, that compound can be stored for later use, or preferably, but not necessarily immediately, hydrolyzed to form the corresponding partial ester (diester). These steps are illustrated in Scheme A, below, using 1H-tetrazole as the catalyst, wherein "n" is an integer 1 through 10, ROH that is an alcohol having a molecular weight of about 250 or less such as a preferred $C_4$–$C_{10}$ alkyl alcohol or $C_4$–$C_{10}$ cycloalkyl alcohol, $(R^1)_3N$ is a tertiary amine, YOH is HOH, ROH or $R^2OH$, and $R^2OH$ is a $C_1$–$C_8$ primary alkyl, primary aralkyl alcohol or phenol.

Scheme A

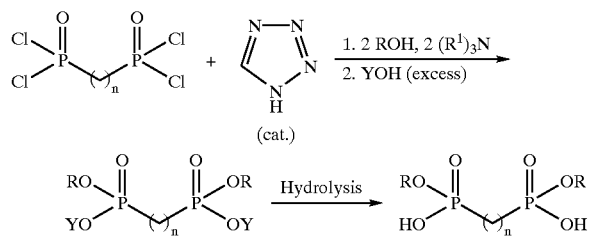

A contemplated compound contains two phosphonate esters. Current nomenclature refers to such compounds as "bisphosphonic acid" esters, although "diphosphonic acid" esters can also be used.

A contemplated alcohol has a molecular weight of less than about 250 Daltons (Da), preferably less than about 200 Da, and more preferably about 75 to about 150 Da. Exemplary alcohols include (tri-$C_1$–$C_4$ alkyl)silyl $C_3$–$C_8$ alkyl alcohols such as 3-(trimethylsilyl)-1-propanol, 4-(trimethylsilyl)-1-butanol and 8-(trimethylsilyl)-1-octanol, polyfluorinated alcohols such as 1H,1H-heptafluoro-1-butanol, 1,1,2,2,3,3,4,4-octafluoro-1-pentanol, 1H,1H-pentafluoro-1-propanol, 2,2,3,3-tetrafluoro-1-propanol, 3-(perfluorohexyl)-1-propanol and 2H-hexafluoro-2-propanol, and $C_4$–$C_{10}$ alkyl alcohol or $C_4$–$C_{10}$ cycloalkyl alcohols that include n-butanol, sec-butanol, iso-butyl alcohol, amyl alcohol, sec-amyl alcohol, 3-pentanol, iso-amyl alcohol, tert-amyl alcohol, neo-pentyl alcohol, cyclohexanol, 3-methylcyclohexanol, hexanol, 2-methyl-1-pentanol, 4-methyl-2-pentanol, 2-ethyl-1-butanol, 1-octanol, 2-ethyl-1-hexanol, 2,4,4-trimethylpentanol, decanol and the like that are preferably other than tertiary and most preferably primary alcohols. Phenyl ring-containing alcohols having six to ten carbon atoms are also contemplated such as phenol, the cresols, the xylenols, (phenols), as well as benzyl alcohol, 2-phenylethanol, cumenol and thymol (aralkyl alcohols). Of the above alcohols, use of 2-ethyl-1-hexanol and 2,4,4-trimethylpentanol is particularly preferred.

The alkylene group between the two phosphorus atoms is a mono- or oligomethylene group [$(-CH_2-)_n$, in which n is an integer that is one to ten] so that the alkylene group is referred to as a $C_1$–$C_{10}$ alkylene group and the compound is a $C_1$–$C_{10}$ alkylenebisphosphonic acid. That alkylene group that links the two phosphorus atoms is preferably methylene or ethylene, and is most preferably methylene, so that n is preferably 1 or 2, and is most preferably 1. Of course, if bisphosphonic acid esters were present that contained a mixture of $C_1$–$C_{10}$ alkylene groups, "n" could be an average value of two or more integers.

A contemplated reaction is carried out under "mild" conditions in that the esterification reaction can be carried out at a temperature of just above the freezing point of the reaction medium solvent to about 110° C. and at atmospheric pressure., The ester-forming reactions are preferably carried out in an aromatic hydrocarbon solvent such as benzene or toluene, whose freezing points are about 5° C. and about −95° C., respectively. The reaction is preferably carried out at ambient room temperature in a dry, inert atmosphere such as under argon or nitrogen.

A contemplated reaction to form a P,P'-diester of methylenebisphosphonic acid is carried out in the presence of a catalytic amount of an aromatic cyclic amine that can also be referred to as a cyclic aromatic amine. That is, the amine is aromatic, it is cyclic and the amine nitrogen is part of the cyclic ring structure, as compared to being a substituent.

Preferably also, the cyclic aromatic amine is monocyclic and contains 5 or 6 atoms in the ring. Multi-ringed catalysts can also be used such as quinoline, isoquinoline and the like, but are not preferred. A preferred catalyst has a $pK_b$ value in excess of about 7, more preferably, the $pK_b$ value is in excess of about 8. Most preferably, the $pK_b$ value is in excess of about 9.

Preferably, that amine is an alpha-effect cyclic aromatic amine. An alpha-effect nucleophile contains an atom with a lone electron pair adjacent to the nucleophilic center as exemplified by 1H-tetrazole and 1H-1,2,3-triazole. If there is an atom containing one or more unshared electron pairs adjacent to the attacking atom on a nucleophile, the nucleophilicity of the attacking atom appears to be enhanced by that lone electron pair located in a position alpha (adjacent) to the nucleophilic atom. [J. March, *Advanced Organic Chemistry: Reactions, Mechanisms and Structure*, 4th ed., John Wiley & Sons, N.Y. (1992) pp. 351–352.] Thus, a contemplated alpha-effect cyclic aromatic amine contains a nucleophilic nitrogen atom and another nitrogen, an oxygen, a sulfur or some other atom that can provide a lone electron pair to the nucleophilic nitrogen. Although the basis is not understood, the alpha-effect cyclic aromatic amines provide excellent yields of the desired P,P'-diesters along with enhanced selectivity; i.e., only one product is formed rather than a mixture containing the desired P,P'-diester product and minimal, but identifiable amounts of side products such as triesters.

Illustrative cyclic aromatic amine catalysts and their parenthesized $pK_b$ values include imidazole (7.01), N-methylimidazole (7.05), N-ethylimidazole (6.7), 4-(dimethylamino)pyridine (4.3), histamine hydrochloride (7.96, 4.25), 1H-1,2,3-triazole (12.82), 1H-1,2,4-triazole (11.7), pyridine (8.77), 1H-tetrazole (9.13), 1-acetylimidazole (10.4), pyrazole (11.52), isoxazole (12.7), thiazole (10.56), pyridazine (11.9), pyrimidine (12.9), pyrazine (13.63), 1,3,5-triazine, 1,2,4-triazine, 1,2,3-triazine, quinoline (9.15), isoquinoline (8.86), cinnoline (11.36), phthalazine (10.61), quinoxaline (13.4) and quinazoline (10.69).

Of the cyclic aromatic amines, the alpha-effect cyclic aromatic amines 1H-1,2,3-triazole and 1H-tetrazole are preferred. The 1H-tetrazole compound is commercially available in solid form (Aldrich Chemical Co., Milwaukee, Wis.) and as a 0.45 M solution in acetonitrile (Fluka, Milwaukee, Wis.). Both materials appear to be equally effective as catalysts herein.

The 1H-tetrazole-catalyzed esterification of methylenebis (phosphonic dichloride) was investigated in a variety of aprotic solvents such as aromatic (benzene, toluene or xylene), chlorinated hydrocarbon ($CH_2Cl_2$ and $CHCl_3$), and polyether (diglyme) solvents as illustrative of preferred catalysts. The aromatic solvents afforded the highest yields and best purity. Toluene with its lower vapor pressure and toxicity is a particularly preferred solvent.

Yields were significantly lower with chlorinated hydrocarbon solvents and product purity was lowered by the presence of non-phosphorus-containing hydrocarbon by products. The greatest fraction of non-phosphorus-containing impurities was obtained when diglyme (2-methoxyethyl ether) was used as the solvent. The presence of these impurities and high boiling point make diglyme the least attractive solvent candidate of those examined.

The base of a contemplated reaction is preferably a tertiary amine that is preferably soluble in the reaction solvent, water-soluble and sterically hindered, although water-soluble bases such as carbonate or phosphate salts can also be used. Exemplary tertiary amines include triisopropylamine, triethylamine, diisopropylethylamine, tripropylamine, tributylamine, quinuclidine, 1,8-bis (dimethylamino)naphthalene, pyridine, 4-dimethyl-aminopyridine, 1H-tetrazole itself and the like.

The synthesis of $C_1$–$C_{10}$ alkylenebis phosphonic ester acid chloride is carried out using about two moles of alcohol per mole of acid chloride, so an excess of alcohol can be present. However, the reaction is preferably carried out using slightly less than two moles of the alcohol to one mole of the acid chloride to prevent the formation of the triester. The reaction preferably is run using about a 1.85:1 to about a 1.99:1 mole ratio of alcohol to acid chloride, with a 1.98:1 mole ratio of alcohol to acid chloride being typically used here. The formation of a small amount of the parent acid or the monoester is not a concern because both are sufficiently water-soluble so that if formed, either partitions into the aqueous phase when the reaction is quenched.

In one more specific aspect of the invention, symmetric $C_1$–$C_{10}$ alkylenebisphosphonic acid partial esters are prepared in high yield and high purity from the corresponding acid chloride using a facile two-step, one-pot process. The first step in the synthesis utilizes 1H-tetrazole to catalyze the regio-selective condensation of $C_1$–$C_{10}$ alkylenebis (phosphonic dichloride) with two equivalents of an alcohol that has a molecular weight of less than about 250 Daltons such as a preferred $C_4$–$C_{10}$ alkyl or cycloalkyl alcohol under mild, anhydrous, basic conditions to form a corresponding $C_1$–$C_{10}$ alkylenebisphosphonic ester acid chloride. In the second step, the partial ester is formed directly when the unreacted P—Cl groups are quenched with water, as is shown in Scheme 1, below, using 1H-tetrazole as illustrative and wherein R is an alcohol that has a molecular weight of less than about 250 Daltons, $(R^1)_3N$ is a tertiary amine and "n" is an integer 1 through 10. This synthesis does not require chromatographic or acid-base extractive purification, and offers substantial advantages over the currently used carbodiimide-promoted coupling route.

Scheme 1

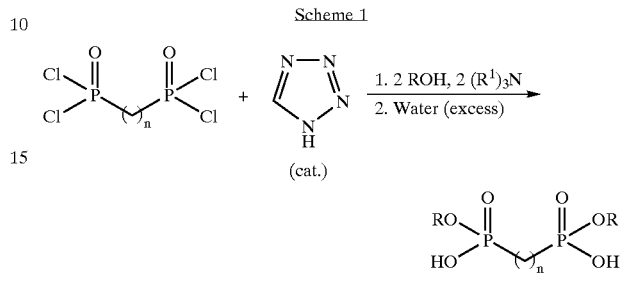

Features of the process important for successfully obtaining the desired product in high purity include careful control of reagent stoichiometry and reaction conditions, use of anhydrous solvents, and slow simultaneous addition of alcohol and hindered base to the acid chloride.

Advantages of the synthetic procedure shown in Scheme 1 over existing preparative methods [Chiarizia et al., *Solv. Extr. Ion Exch.*, 14:773–792 (1996); Horwitz et al., *React. Funct. Polym.*, 22:25–36 (1997); and Griffith-Dzielawa et al., *Synth. Commun.*, 30:2121–2132 (2000)] include: higher yields, shorter reaction times, milder conditions, less expensive and less toxic starting reagents, smaller secondary waste streams and simpler isolation and purification procedures. Further, the reaction is easily scaled-up and the amine starting reagents can be recovered by neutralizing the aqueous waste with an inexpensive inorganic base like NaOH.

Another more specific aspect of the invention contemplates preparation of symmetric $C_1$–$C_{10}$ alkylenebisphosphonic acid partial esters from the corresponding homoleptic $C_1$–$C_{10}$ alkylenebisphosphonates; i.e., alkylenebisphosphonates having four identical ligands as ester groups, or the mixed dimethyl $C_1$–$C_{10}$ alkylenebisphosphonate esters by selective deprotection of the corresponding tetraesters. Where methanol is used as the second alcohol, YOH, discussed before, these compounds can also be named as the $C_1$–$C_{10}$ alkylenebis(alkyl methyl phosphonates), with the preferred homoleptic methylenebisphosphonates being abbreviated $R_4$[MBP], and the preferred alkyl methyl methylenebisphosphonates being abbreviated $R_2Me_2$[MBP].

These partial ester compounds are prepared by the cyclic aromatic amine-catalyzed esterification of $C_1$–$C_{10}$ alkylenebis(phosphonic dichloride) using a procedure similar to that described above for the synthesis of P,P'-dialkyl alkylenebisphosphonic acids. In one modified procedure, excess methanol is used in the second step in place of water to quench the reaction, as is shown in Scheme 2, below, again using 1H-tetrazole as illustrative and wherein R, $(R^1)_3N$ and "n" are as before, and trimethylsilyl bromide (TMSBr) or hydrochloric acid are preferably used for the hydrolysis step.

Scheme 2

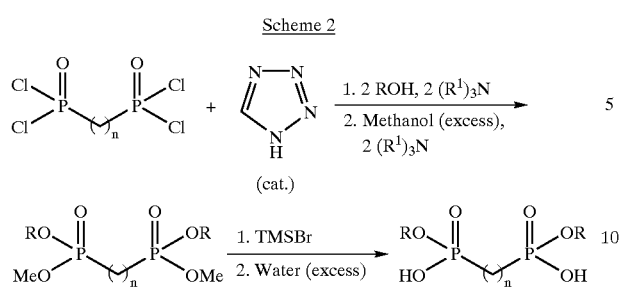

Alternatively, partial ester compounds are prepared by the cyclic aromatic amine-catalyzed esterification of $C_1$–$C_{10}$ alkylenebis(phosphonic dichloride) using an excess of the first alcohol (ROH) to form the homoleptic tetraester that is then selectively cleaved to form the partial ester, as is shown in Scheme 3, below, using 1H-tetrazole as illustrative, and wherein R. $(R^1)_3N$ and "n" are as before, and hydrolysis is preferably carried out using hydrochloric acid or trimethylsilyl bromide. Substantially any secondary or tertiary amine catalyst can be used in the preparation of a tetraester.

Scheme 3

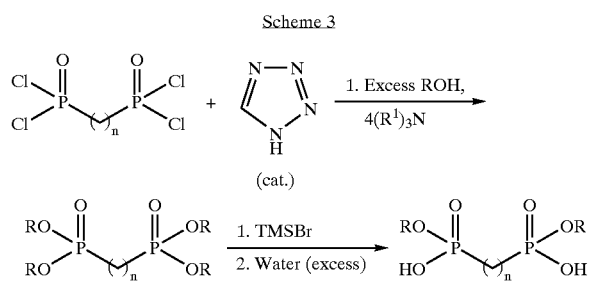

A number of primary alkyl, cyclic secondary alkyl, aromatic and silicon containing alcohols have been successfully utilized to prepare illustrative mixed and homoleptic methylenebisphosphonates, $R_2Me_2[MBP]$ and $R_4[MBP]$. Bisphosphonic acid partial esters can be prepared in very high purity from both types of tetraester. The tetraesters are amenable to separation and purification by chromatography and a variety of conditions can be used to elaborate the bisphosphonate precursor to the desired partial ester. This approach is one method of choice when the resulting acids are water-soluble or the product obtained by the procedure shown in Scheme 1 is a complex mixture.

A two-step reaction producing mixed diesters of monophosphonic acids has been reported for alkyl and aryl substituents. Zhao et al., *Tetrahedron*, 49:363–368 (1993). The method described herein for the preparation of a bisphosphonic acid mixed tetraester builds upon those published conditions. Methods are also known for forming a monophosphonic monoester from a corresponding monophosphonic acid diester. McKenna et al., *J. Chem. Soc. Chem. Commun.*, 739 (1979); McKenna et al., *J. Org. Chem.*, 46:4573–4576 (1981), and McKenna et al., *Tetrahedron Lett.*, 2:155–158 (1977). Mixed tetraesters of bisphosphonic acids synthesized by the reactions described herein have not been reported, although a monoester triacid has been prepared by a similar route. Lesiak et al., *J. Org. Chem.*, 63:1906–1909 (1998).

Methods for selective deprotection of tetraesters to the corresponding partial esters of dichloromethylenebisphosphonic acid using tertiary and secondary amines as dealkylating reagents have been reported. That deprotection however requires the presence of an activating group to instigate the reaction. Vepsäläinen et al., *Tetrahedron*, 51:6805–6818 (1995) and Vepsäläinen et al., *Tetrahedron Lett.*, 37:3533–3536 (1996). Hydrolysis of symmetric methylenebisphosphonic acid tetraesters with acids, bases and silyl intermediates are generally not selective, producing a mixture of products requiring chromatographic or efficient fractional crystallization for separation. Vepsäläinen et al., *Tetrahedron Lett.*, 34:4551–4554 (1993).

Partial dealkylation (hydrolysis) of bisphosphonates can be achieved using a variety of deprotecting reagents. Reagents that have been used to remove phosphonate ester groups include trimethylsilyl halides, [Morita et al., *Bull. Chem. Soc. Japan*, 54:267–273 (1981); and McKenna et al., *Tetrahedron Lett.*, 2:155–158 (1977)] mineral acids [Petrow et al., *J. Gen. Chem. USSR* (Engl. Transl.), 39:809–811 (1969)], lithium halides [Krawczyk, *Synth. Commun.*, 27:3151–3161 (1997)], and tertiary as well as secondary amines [Vepsäläinen et al., *Tetrahedron*, 51:6805–6818 (1995)]. Under selected conditions, these reagents can be used for either complete or selective hydrolysis of bisphosphonates.

The phosphonate salts formed when lithium halides or amines are used for the dealkylation process can be readily converted to the acid via acidification with strong acid or ion exchange chromatography. The selective dealkylation of mixed dimethyl esters using hydrochloric acid or trimethylsilyl bromide was focused on here because of the simplicity of the work up required to obtain the desired partial esters by this route. The selective deprotection achieved by both reagents exploits the greater reactivity of the methyl group that is hydrolyzed much more rapidly than most other alkyl or aralkyl groups of interest.

The trimethylsilyl bromide, TMSBr, dealkylation proceeds under mild conditions and all volatile products are removed under reduced pressure. The trimethylsilyl esters formed in this reaction are readily hydrolyzed to the desired acid. The hydrolysis with HCl is more difficult to control and the final product may contain the starting alcohol as an impurity. This product can be suitable for use as technical grade extractant.

The performance of the products formed by this condensation reaction sequence is as good if not better than carbodiimide-promoted coupling products.

The procedure has general synthetic applicability for the preparation of a variety of partial esters of a $C_1$–$C_{10}$ alkylenebis(phosphonic acid). A number of primary alkyl, cyclic secondary alkyl and silicon containing alcohols have been successfully utilized in this procedure.

The partial esters are of interest as metal ion complexing reagents and can be used in organic solution as solvent extraction reagents [Chiarizia et al., *Solvent Extr. Ion Exch.*, 14:773–792 (1996)] or coated on a solid support as an extraction chromatographic material [Horwitz et al., *Reactive and Functional Polymers*, 33:25–36 (1997); U.S. Pat. Nos. 5,651,883 and 5,851,401].

Reaction of phenol or a fluorine containing alcohol with methylenebis(phosphonic dichloride) produces a mixture that contains substantial amounts of all possible bisphosphonate esters. Bisphosphonic acid partial esters of alcohols that yield complex mixtures by the reaction sequence shown in Scheme 1 are best prepared from the exemplary P,P'-dialkyl-P,P'-dimethyl alkylenebisphosphonates, or the homoleptic tetraesters, whose synthetic pathways are illustrated in Schemes 2 and 3. The tetraesters are amenable to separation and purification by chromatography and a variety of conditions can be used to elaborate the dimethyl precursor to the desired bisphosphonic acid.

The tetrazole-catalyzed condensation of methylenebis (phosphonic dichloride) was used successfully for the preparation of P,P'-bis(2-ethylhexyl) P,P'-dimethyl methylenebisphosphonate, $EH_2Me_2[MBP]$. The mixed methyl ester has been shown to be a viable precursor to the commercial Dipex® extractant, $H_2DEH[MBP]$. The final conversion of $EH_2Me_2[MBP]$ to $H_2DEH[MBP]$ exploits the different reactivity of the methyl and 2-ethylhexyl esters. In some cases, the mixed methyl ester precursor can provide the best synthetic route to the analytically pure reagent.

A number of primary alkyl, cyclic secondary alkyl, fluoroalkyl, aromatic and silicon containing alcohols have been successfully utilized to prepare exemplary methylenebisphosphonates, $R_2Me_2[MBP]$ and $R_4[MBP]$. Bisphosphonic acid partial esters can be prepared in very high purity from both types of tetraester. The tetraesters are amenable to separation and purification by chromatography and a variety of conditions can be used to elaborate the bisphosphonate precursor to the desired partial ester. This approach is the method of choice when the resulting acids are water-soluble or the product obtained by the procedure shown in Scheme 1 is a complex mixture.

Alkylenebis(alkyl methyl phosphonate) compounds are prepared by the 1H-tetrazole catalyzed esterification of methylenebis(phosphonic dichloride) using a procedure similar to that described above for the synthesis of P,P'-dialkyl alkylenebisphosphonic acids of Scheme 1. In this procedure, excess methanol is used in the second step in place of water to quench the reaction, as is shown in Scheme 2.

The P,P'-dialkyl-P,P'-dimethyl $C_1$–$C_{10}$ alkylenebisphosphonate that is formed is illustratively demethylated by using trimethylsilyl bromide (TMSBr), and the resulting trimethylsilyl diester is reacted with water to form the hydrolyzed partial ester. The demethylation using stoichiometric amounts of trimethylsilyl bromide is generally selective. This selectivity, however, can be lost in the deprotection of fluoroalkyl-containing esters and when a large excess of the TMSBr is used. A typical preparation is described hereinafter for the synthesis of $H_2DEH[MBP]$. Several other symmetric methylenebisphosphonic acid partial esters were prepared following this procedure by replacing the 2-ethyl-1-hexanol with 1-butanol, cyclohexanol, phenol, 1H, 1H-heptafluoro-1-butanol or 3-trimethylsilyl-1-propanol.

Comparison of Synthetic Methods

Yields of phosphonic acid, partial esters and tetraesters prepared using syntheses illustrated in the reaction schemes described previously are provided in the Table below for the illustrative methylenebisphosphonic acid compounds.

| ALCOHOL [R or $R^2$] | Yields Obtained from 1H-Tetrazole-Catalyzed Reactions (%) | | | |
|---|---|---|---|---|
| | $H_2DR^2$ [MBP] * | $Me_2R^2{}_2$ [MBP] | $H_2DR^2$ [MBP] ** | $R^2{}_4$ [MBP] |
| 1-Butanol | — | 85 | 85 | 98 |
| 1-Hexanol | 84 | 85 | 82 | 90 |
| Cyclohexanol | 84 | 70 | 70 | 85 |
| 1-Octanol | 94 | — | — | — |
| 2-Ethyl-1-Hexanol | 92 | 82 | 82 | 85 |
| 2,4,4-Trimethyl-1-pentanol | 93 | — | — | — |
| 3-(Trimethyl-silyl)-1-propanol | 90 | 65 | 65 | 83 |
| Phenol | — | 25 | 25 | 85 |
| 1H,1H-Heptafluoro-1-butanol | — | 30 | 10 *** | 82 |

* Synthesized by quenching with water.  Synthesized by deprotection with TMSBr. * Not isolated.

Syntheses

Without further elaboration, it is believed that one skilled in the art can, using the preceding description, utilize the present invention to its fullest extent. The following preferred specific embodiments are, therefore, to be construed as merely illustrative, and not limiting of the remainder of the disclosure in any way whatsoever.

All reagents supplied by Aldrich were used as received without further purification. Methylenebis(phosphonic dichloride) was handled under anhydrous conditions. All glassware was oven dried at 120° C. and anhydrous solvents were dispensed from Aldrich Sure-Seal bottles (Aldrich Chemical Co., Milwaukee, Wis.). Flash column chromatography was performed using silica gel (32–63 μm, Selecto, Fisher Scientific, Pittsburgh, Pa.).

EXAMPLE 1

Preparations via Scheme 1

The bisphosphonic acid compounds discussed below were prepared by the 1H-tetrazole-catalyzed esterification of methylenebis(phosphonic dichloride) using a procedure similar to that reported by Zhao and Landry for the synthesis of mixed esters of monophosphonic acids. [Zhao et al., Tetrahedron, 49:363–368 (1993).] A representative preparation is described below for $H_2DEH[MBP]$, P,P'-bis(2-ethylhexyl)methylenebisphosphonic acid or Dipex® extractant. Several other symmetric partial esters of methylenebisphosphonic acid were prepared following this procedure by replacing the 2-ethyl-1-hexanol with 1-hexanol, cyclohexanol, 1-octanol, 2,4,4-trimethyl-1-pentanol or 3-trimethylsilyl-1-propanol. This procedure has been scaled-up by a factor of five without any complications. Yields typically are in the 85–95% range.

Preparation of DIPEX® Extractant or $H_2DEH[MBP]$

Methylenebis(phosphonic dichloride) (1.00 g, 4.00 mmol) and 1H-tetrazole (0.05 g, 0.7 mmol) were placed in a 100 mL Schlenk flask and dissolved in 50 mL of toluene with vigorous stirring under a nitrogen atmosphere. When the dissolution was complete, a solution of 2-ethyl-1-hexanol (1.24 mL, 7.92 mmol) and diisopropylethylamine (1.53 ml, 8.80 mmol) in 20 mL of toluene was added drop-wise through an addition funnel over a 120 minute period. After stirring overnight (about 16–18 hours) at room temperature under an atmosphere of nitrogen, the reaction mixture was quenched with 30 mL of water. The mixture was stirred for 15 minutes, transferred to a separatory funnel and the organic phase washed twice with 0.1 M HCl. The tetrazole and amine partitioned into the aqueous phase as their respective salts, whereas the desired product remained in the organic phase. The Dipex® extractant product was obtained as a colorless oil after removing the organic solvent under reduced pressure at 60° C. Yield 92%. Equiv. Wt.: calc. 200.2 g/mol, found 199.2 g/mol. Anal.: calc. for $C_{17}H_{38}O_6P_2$: C, 50.99; H, 9.56, found: C, 51.37; H, 9.89. $^1$H NMR (CDCl$_3$, δ): 10.46 (s, 2 H, OH), 3.97 (m, 4 H, OCH$_2$) 2.43 (t, 2 H, $J_{P,H}$=21.8 Hz, P—CH$_2$—P), 1.55 (m, 2 H, CH), 1.22–1.42 (m, 16 H, CH$_2$), 0.87 (m, 12 H, CH$_3$); $^{31}$P NMR (CDCl$_3$, δ): 19.45 (s).

If excess alcohol is used, the $^1$H NMR spectrum of the product shows the presence of a small amount of another phosphorus containing species, presumably the tri-ester, and unreacted 2-ethyl-1-hexanol. These compounds are not easily removed, but neither significantly interferes with the product's performance as an extractant. This product is suitable for use as technical grade Dipex® extractant.

Excessive foaming can occur if the product is washed multiple times with water. Washing with 0.1–0.2 M HCl obviates the foaming problem and ensures that unreacted amine and tetrazole partition into the aqueous phase. Further purification of an alcohol-containing product can be achieved, if so desired, by the conventional acid-base extractive procedure that is used to purify Dipex® prepared by the carbodiimide-promoted coupling route. Chiarizia et al., *Solv. Extr. Ion Exch.*, 14:73–792 (1996).

The tetrazole-catalyzed esterification of methylenebis (phosphonic dichloride) with 2-ethyl-1-hexanol as shown in Scheme 1 was also carried out under anhydrous conditions in an NMR tube using benzene-d$_6$ as the solvent and tetrazole as the base. The reaction was followed by $^{31}$P and $^1$H NMR spectroscopy. Two principal reaction intermediates were observed and identified on the basis of chemical shifts and splitting patterns as methylenebis(2-ethylhexyl phosphonic chloride), Cl$_2$EH$_2$[MBP], and 2-ethylhexyl methylenebisphosphonic trichloride, Cl$_3$EH[MBP].

As the reaction proceeded, the $^{31}$P NMR spectrum showed the disappearance of the singlet at δ 22.07 due to methylenebis(phosphonic dichloride), CH$_2$(POCl$_2$)$_2$, as well as the appearance of two doublets of equal intensity at δ 25.45 and 21.27 (J=39.4 Hz), which were assigned to the ester tri-acid chloride, Cl$_3$EH[MBP]. During the early stages of the reaction, the CH$_2$(POCl$_2$)$_2$ singlet disappeared at approximately the same rate as the Cl$_3$EH[MBP] doublets appeared. During the latter stages of the reaction, the doublets disappeared at about the same rate as two singlets of nearly equal intensity appeared at δ 24.61 and 24.37. Those new singlets were attributed to the formation of the diester di-acid chloride Cl$_2$EH$_2$[MBP] that exists in solution as two diastereomers.

The $^1$H NMR spectrum was less informative because of its complexity, but the presence of 2-ethyl-1-hexanol as well as several phosphorus-containing esters was evident. The signals in the P—CH$_2$—P and O—CH$_2$ chemical shift regions change in intensity as the reaction proceeds. The $^1$H resonances associated with the P—CH$_2$—P groups of the phosphorus-containing intermediates appear about 0.3 ppm down field from the corresponding signal in the target diester di-acid. This down field shift is consistent with the presence of electron withdrawing chloro groups on the phosphorus atoms of the bisphosphonate.

No attempt was made to isolate the acid chloride intermediates. A report in the Russian literature describes the isolation of dicyclohexyl ethylenebisphosphonochloridate that was prepared by reacting tetracyclohexyl ethylenebisphosphonate with phosphorus pentachloride. Petrow et al., *J. Gen. Chem. USSR* (Engl.Transl.) 39:809–811 (1969).

Attempts to purify the diester di-acid chloride precursor resulted in decomposition, but the impure product was successfully converted to dicyclohexyl ethylenebisphosphonic acid by hydrolysis with water.

Attempts to prepare dicyclohexyl methylenebisphosphonochloridate by the above Petrow et al. method were unsuccessful. The isolated product was crude dicyclohexyl (dichloromethylene)-bisphosphonochloridate. This crude acid chloride was isolated and hydrolyzed to the acid with water. Dicyclohexyl methylenebisphosphonic acid, H$_2$DcH [MBP], was prepared by the hydrolysis of tetracyclohexyl methylenebisphosphonate with hydrochloric acid. In contrast, H$_2$DcH[MBP] was prepared directly from the acid chloride precursor formed in step 1 of Scheme 1 by quenching the reaction with water in step 2.

Characterization of Compounds Prepared as Shown in Scheme 1

The purity of the compounds was established by $^1$H and $^{31}$P NMR spectroscopy, potentiometric titration, elemental analysis and mass spectroscopy. $^1$H and $^{31}$P data were recorded on a Varian VXR 400 MHz spectrometer using CDCl$_3$ as the solvent. The δ values reported in parts per million (ppm) are relative to internal CHCl$_3$ and external 85% H$_3$PO$_4$, respectively, unless otherwise stated. Equivalent weights were determined by titration with 0.1 M NaOH in an isopropanol-toluene mixture using an Orion EA 940 pH meter. Combustion analyses were performed by Galbraith Laboratories, Inc., Knoxville, Tenn. High-resolution fast atom bombardment (HRFAB) mass spectroscopy was performed by the Washington University Mass Spectrometry Resource, Department of Chemistry, St. Louis, Mo. 63130.

Methylenebis (phosphonic dichloride), CH$_2$(POCl$_2$)$_2$: $^1$H NMR (Benzene-d$_6$, δ): 4.09 (t, 2 H, $J_{P,H}$=21.6 Hz, P—CH$_2$—P); $^{31}$P NMR (Benzene-d$_6$, δ): 22.07 (s).

P,P'-Di-n-hexyl methylenebisphosphonic acid, H$_2$DH [MBP]: This compound was obtained as a white solid in 84% yield. $^1$H NMR (CDCl$_3$, δ): 10.89 (s, 2 H, OH), 4.06 (dt, 4 H, $J_{P,H}$=J=6.8 Hz, OCH$_2$), 2.42 (t, 2 H, $J_{P,H}$=21.6 Hz, P—CH$_2$—P), 1.65 (p, 4 H, J=6.9 Hz, OCH$_2$CH$_2$CH$_2$), 1.22–1.38 (m, 12 H, CH$_2$), 0.88 (t, 6 H, J=6.8 Hz, CH$_3$); $^{31}$P NMR (CDCl$_3$, δ): 19.36 (s). Equiv. Wt.: calc. 172.2 g/mol, found 174.0 g/mol. Anal.: calc. for C$_{13}$H$_{30}$O$_6$P$_2$: C, 45.35; H, 8.78, found: C, 45.32; H, 9.19. M.P. 39.5–40.5° C.

P,P'-Dicyclohexyl methylenebisphosphonic acid, H$_2$DcH [MBP]: This compound reported in the literature to be an oil [Petrow et al., *J. Gen. Chem. USSR* (Engl. Transl.) 39:809–811 (1969)] was isolated as a white solid in 84% yield. $^1$H NMR (CDCl$_3$, δ): 9.25 (s, 2 H, OH), 4.50 (m, 2 H, CH), 2.43 (t, 2 H, $J_{P,H}$=21.6 Hz, P—CH$_2$—P), 1.15–2.02 (m, 20 H, CH$_2$); $^{31}$P NMR (CDCl$_3$, δ): 18.35 (s). Equiv. Wt. : calc. 170.1 g/mol, found 179.5 g/mol. Anal.: calc. for C$_{13}$H$_{26}$O$_6$P$_2$: C, 45.89; H, 7.70, found: C, 46.33; H, 8.01. M.P. 133–135° C.

P,P'-Di-n-octyl methylenebisphosphonic acid, H$_2$DO [MBP]: This compound was isolated as a white solid in 94% yield. $^1$H NMR (CDC$_3$, δ): 10.11 (s, 2 H, OH), 4.06 (dt, 4 H, $J_{P,H}$=J=6.9 Hz, OCH$_2$), 2.42 (t, 2 H, $J_{P,H}$=21.6 Hz, P—CH$_2$—P), 1.65 (p, 4 H, J=7.0 Hz, OCH$_2$CH$_2$), 1.20–1.39 (m, 20 H, CH$_2$), 0.88 (t, 6 H, J=7.0 Hz, CH$_3$); $^{31}$P NMR (CDCl$_3$, δ): 19.36 (s). Equiv. Wt.: calc. 200.2 g/mol, found 204.0 g/mol. M.P. 54–56° C. (lit. 55° C.).[Gorican et al., *J. Chem. Soc.*,513–515(1964)]

P,P'-Di(2,4,4-trimethylpentyl)methylenebisphosphonic acid, H$_2$DTMP[MBP]: This C$_8$ ester of methylenebisphosphonic acid was isolated as a white solid in 93% yield. $^1$H NMR (CDCl$_3$, δ): 10.44 (s, 2 H, OH), 3.72–3.92 (m, 4 H, OCH$_2$), 2.42 (t, 2 H, J$_{P,H}$=21.8 Hz, P—CH$_2$—P), 1.83 (m, 2 H, CH), 0.97–1.28 (m, 4 H, CH$_2$), 0.97 (d, 6 H, J=6.8 Hz, CHCH$_3$), 0.89 (s, 18 H, CCH$_3$); $^{31}$P NMR (CDCl$_3$, δ): 19.30 (s). Equiv. Wt.: calc. 200.2 g/mol, found 207.4 g/mol. Anal. calc. for C$_{17}$H$_{38}$O$_6$P$_2$: C, 50.99; H, 9.56, found: C, 51.14; H, 10.00. M.P. 67–70° C.

P,P'-Di[3-(trimethylsilyl)propyl]methylenebisphosphonic acid, H$_2$DTMSP[MBP]: This compound was obtained as a white solid in 90% yield. $^1$H NMR (CDCl$_3$, δ): 10.31 (s, 2 H, OH), 4.01 (dt, 4 H, J$_{P,H}$=J=7.2 Hz, OCH$_2$), 2.43 (t, 2 H, J$_{P,H}$=21.6 Hz, P—CH$_2$—P), 1.65 (m, 4 H, OCH$_2$CH$_2$), 0.48 (m, 4 H, OCH$_2$CH$_2$CH$_2$), –0.01 (s, 18 H, CH$_3$); $^{31}$P NMR (CDCl$_3$, δ): 19.28 (s). Equiv. Wt.: calc. 202.3 g/mol, found 203.9 g/mol. M.P. 39–41° C. (lit. 32–34° C.).[Griffith-Dzielawa et al., *Synth. Commun.*, 30: 2121–2132(2000)]

EXAMPLE 2

Preparations via Scheme 2

The dimethyl ester precursors prepared by this procedure generally are isolated as hydrates. The yields obtained using this procedure can vary widely with the nature of the starting alcohol and the complexity of the mixture obtained as the crude product. Yields via this route with fluorine containing alcohols are unacceptably low (about 10%). The preparation of methylenebisphosphonic acid partial esters of a fluorinated alcohol is best achieved by dealkylation of the corresponding homoleptic tetraesters; i.e., the methylenebis (dialkyl phosphonates), as discussed hereinafter.

Preparation of DIPEX® Extractant or H$_2$DEH[MBP]

Methylenebis(phosphonic dichloride) (1.00 g, 4.00 mmol) and 1H-tetrazole (0.05 g, 0.7 mmol) were placed in a 100 ml Schlenk flask and dissolved in 50 mL of benzene with vigorous stirring under a nitrogen atmosphere. When the dissolution was complete, a solution of 2-ethyl-1-hexanol (1.25 mL, 8.00 mmol) and diisopropylethylamine (1.53 mL, 8.80 mmol) in 20 mL of benzene was added drop-wise through an addition funnel over a 2 hour period. After stirring overnight (about 16–18 hours) at room temperature under an atmosphere of nitrogen, a solution of methanol (0.40 mL, 10.0 mmol) and diisopropylethylamine (1.53 mL, 8.80 mmol) in 20 mL of benzene was added slowly over a 20 minute period. The resulting solution was stirred 15 minutes at room temperature under an atmosphere of nitrogen, concentrated in vacuo and the resulting residue suspended in hexane. The diisopropylethylammonium chloride and tetrazonium chloride salts formed as reaction by-products were removed by filtration using a Hirsch funnel and the solvent was again removed in vacuo. The crude product, a light yellow oil, was purified by flash chromatography (25:75 v/v hexane/acetone; R$_f$=0.80, second band). Methylenebis-(2-ethylhexyl methyl phosphonate), a novel compound isolated as a hydrate, was obtained as a colorless oil in 82% yield. (Me$_2$EH$_2$[MBP]×½ H$_2$O): $^1$H NMR (CDCl$_3$, δ): 4.01 (m, 4 H, OCH$_2$), 3.82 & 3.80 (d, 6 H, J$_{P,H}$=11.2 Hz, OCH$_3$), 2.45 (t, 2 H, J$_{P,H}$=21.2 Hz, P—CH$_2$—P), 1.70 (s, br, 1 H, H$_2$O), 1.58 (m, 2 H, CH), 1.23–1.47 (m, 16 H, CH$_2$), 0.90 (m, 12 H, CH$_3$); $^{31}$P NMR (CDCl$_3$, δ): 21.01(s) & 20.97(s). Anal. calc. for C$_{19}$H$_{41}$O$_6$P$_2$. ½ H$_2$O: C, 52.16; H, 9.91, found: C, 52.29; H, 9.70.

Trimethylsilyl bromide (1.19 mL, 1.38 g, 9.00 mmol) was added with stirring to a solution of methylenebis(2-ethylhexyl methyl phosphonate) (1.29 g, 3.00 mmol) in 5 mL of CH$_2$Cl$_2$. After stirring for 30 minutes at room temperature, the alkyl bromide by-products and excess bromosilane were removed in vacuo and the reaction was quenched with 5 mL of water. The Dipex® product was obtained as a colorless oil after removing the water under reduced pressure at 60° C. The yield is quantitative. $^{31}$P NMR (CDCl$_3$, δ): 19.43 (s). Equiv. Wt.: calc. 200.2 g/mol, found 203.2 g/mol.

The hydrolysis of Me$_2$EH$_2$ [MBP] by mineral acid was also investigated. Concentrated hydrochloric acid was used under a variety of reaction conditions. Hydrolysis of Me$_2$EH$_2$[MBP] with 8 M HCl at 80° C. for 2 hours produced H$_2$DEH[MBP] in the best yield (90%) with 2-ethyl-1-hexanol as the only impurity in the final product. This product would be suitable for use as technical grade Dipex®.

Characterization of Compounds Prepared as Shown in Scheme 2

The mixed Me$_2$R$_2$[MBP] tetraesters prepared by the procedure shown in Scheme 2, generally were isolated as hydrates. The fluorine containing ester (C$_3$F$_7$CH$_2$)$_2$Me$_2$ [MBP], however, was obtained as an anhydrous compound. The $^{31}$P NMR spectrum of the mixed tetraester contains two singlets, suggesting that two diastereomers are present; an enantiomeric pair and a meso form. This stereochemistry is further confirmed by the $^1$H NMR behavior of the P—CH$_2$—P, —OCH$_3$ and —OCH$_2$— functionalities. These groups show additional splitting due to the presence of the two diastereomers. The existence of the stereoisomers is most evident in the resonance at about 3.8 ppm that arises from the methyl ester groups. Two doublets are readily apparent, one corresponding to the d,l pair of enantiomers and another corresponding to the meso form. Physical separation of the isomers and assignment of the corresponding NMR peaks was not pursued for the mixed tetraesters because the desired final products are the methylenebisphosphonic acid partial esters. The $^{31}$P and $^1$H NMR spectra of the partial esters do not exhibit this splitting. The stereoisomeric forms of the partial esters are not observed in their NMR spectra because the acidic hydrogen atoms undergo rapid exchange on the NMR time scale.

Methylenebis(butyl methyl phosphonate) monohydrate, Me$_2$Bu$_2$[MBP]×H$_2$O: This mixed ester was obtained as a colorless oil in 85% yield after purification by flash chromatography (5:95 v/v CH$_3$OH/CH$_2$Cl$_2$; R$_f$=0.9). $^1$H NMR (CDCl$_3$, δ): 4.11 (dt, 4 H, J$_{P,H}$=J=6.8 Hz, OCH$_2$), 3.81 & 3.80 (d, 6 H, J$_{P,H}$=11.2 Hz, OCH$_3$), 2.46 (t, 2 H, J$_{P,H}$=21.2 Hz, P—CH$_2$—P), 1.67 (p, 4 H, J=6.8 Hz, OCH$_2$CH$_2$), 1.41 (m, 4 H. CH$_2$CH$_3$), 0.94 (t, 6 H, J=7.4 Hz, CH$_2$CH$_3$); $^{31}$P NMR (CDCl$_3$, δ): 21.40 & 21.38 (s). Anal. calc. for C$_{11}$H$_{28}$O$_7$P$_2$: C, 39.52; H, 8.44, found: C, 39.77; H, 8.09. HRMS-FAB (m/z): [M+H]$^+$ calc. 317.1284, found 317.1276.

P,P'-Dibutyl methylenebisphosphonic acid (H$_2$DBu [M9P]): This water soluble acid was obtained as a colorless oil in 85% yield. $^1$H NMR (CDCl$_3$, δ): 8.81 (s, 2 H, OH), 4.11 (dt, 4 H, J$_{P,H}$=J=6.8 Hz, OCH$_2$), 2.45 (t, 2 H, J$_{P,H}$=21.6 Hz, P—CH$_2$—P), 1.68 (p, 4 H, J=6.8 Hz, OCH$_2$CH$_2$), 1.41 (m, 4 H, CH$_2$CH$_3$), 0.95 (t, 6 H, J=7.2 Hz, CH$_2$CH$_3$) ; $^{31}$P NMR (CDCl$_3$, δ): 19.40 (s). Equiv. Wt.: calc. 144.1 g/mol, found 138.8 g/mol.

Methylenebis(hexyl methyl phosphonate) monohydrate, Me$_2$H$_2$[MBP]×H$_2$O: This novel compound was obtained after purification by flash chromatography (5:95 v/v CH$_3$OH/ethyl acetate; R$_f$=0.8) as a colorless oil in 85% yield. $^1$H NMR (CDCl$_3$, δ): 4.10 (dt, 4 H, J$_{P,H}$=J=7.0 Hz, OCH$_2$), 3.81 & 3.80 (d, 6 H, J$_{P,H}$=11.2 Hz, OCH$_3$), 2.45 (t, 2 H, J$_{P,H}$=21.0 Hz, P—CH$_2$—P), 1.87 (s, br, 2 H, H$_2$O ), 1.68 (p, 4 H, J=6.9 Hz, OCH$_2$CH$_2$), 1.24–1.41 (m, 12 H, CH$_2$), 0.89 (t, 6 H, J=7.0 Hz, CH$_3$); $^{31}$P NMR (CDCl$_3$, δ): 21.40 & 21.38 (s). Anal. calc. for C$_{15}$H$_{36}$O$_7$P$_2$: C, 46.15; H, 9.29, found: C, 46.31; H, 8.88. Hydrolysis of the mixed ester to the H$_2$DH[MBP] partial ester was nearly quantitative. Equiv. Wt.: calc. 172.2 g/mol, found 181.2 g/mol.

Methylenebis(cyclohexyl methyl phosphonate) monohydrate, Me$_2$CH$_2$[MBP]×H$_2$O: This mixed ester was obtained as a colorless oil in 85% yield after purification by flash chromatography (25:75 v/v hexane/acetone; R$_f$=0.7). $^1$H NMR (CDCl$_3$, δ): 4.49 (m, 2 H, CH), 3.78 & 3.79 (d, 6 H, J$_{P,H}$=11.4 Hz, OCH$_3$), 2.43 (t, 2 H, J$_{P,H}$=21.0 Hz, P—CH$_2$—P), 1.17–2.06 (m, 20 H, CH$_2$); $^{31}$P NMR (CDCl$_3$, δ): 19.97 & 19.91(s). Anal. calc. for C$_{15}$H$_{32}$O$_7$P$_2$: C, 46.63; H, 8.35, found: C, 46.98; H, 8.19. Hydrolysis of the mixed methyl ester to the H$_2$DcH[MBP] partial ester was quantitative. Equiv. Wt.: calc. 184.2 g/mol, found 174.1 g/mol.

Methylenebis(3-(trimethylsilyl)propyl methyl phosphonate) monohydrate, Me$_2$TMSP$_2$[MBP]×H$_2$O: This silyl-containing ester was obtained as a colorless oil in 65% yield after purification by flash chromatography (20:80 v/v CH$_2$Cl$_2$/acetone; R$_f$=0.8). $^1$H NMR (CDCl$_3$, δ): 4.06 (dt, 4 H, J$_{P,H}$=J=7.2 Hz, OCH$_2$), 3.82 & 3.81 (d, 6 H J$_{P,H}$=11.2 Hz, OCH$_3$), 2.46 (t, 2 H, J$_{P,H}$=21.0 Hz, P—CH$_2$—P), 1.68 (m, 4 H, OCH$_2$CH$_2$), 0.50 (m, 4 H, CH$_2$Si), -.02 (s, 18 H Si(CH$_3$)$_3$); $^{31}$P NMR (CDCl$_3$, δ): 20.93 & 20.91(s). Anal. calc. for C$_{15}$H$_{40}$O$_7$P$_2$Si$_2$: C, 39.98; H. 8.95, found: C, 40.11; H, 9.09. HRMS-FAB (m/z): [M+H]$^+$ calc. 433.1716, found 433.1745. Hydrolysis of the mixed methyl ester to the silyl-containing acid H$_2$DTMSP[MBP] was quantitative. Equiv. Wt.: calc. 202.3 g/mol, found 193.4 g/mol.

Methylenebis(methyl phenyl phosphonate) monohydrate, Me$_2$Ph$_2$[MBP]×H$_2$O: This mixed diaryl ester was obtained as a colorless oil in 25% yield after purification by flash chromatography (30:70 v/v acetone/ethyl acetate; R$_f$=0.5). Me$_2$Ph$_2$[MBP]×H$_2$O was prepared as described above using toluene as the solvent and carrying out the reaction at −78° C. $^1$H NMR (CD$_2$Cl$_2$, δ): 7.16–7.44 (m, 10 H, Ar), 3.88 & 3.87 & 3.80 (d, 6 H, J$_{P,H}$=11.6 Hz, OCH$_3$), 2.761 & 2.75 & 2.747(t, 2 H, J$_{P,H}$=21.2 Hz, P—CH$_2$—P); $^{31}$P NMR (CD$_2$Cl$_2$, δ): 16.70 & 16.60 (s). Anal. calc. for C$_{15}$H$_2$O$_7$P$_2$: C, 48.14; H, 5.39, found: C, 48.01; H, 5.41.

P,P'-Diphenyl methylenebisphosphonic acid, H$_2$DPh [MBP]: This partial diaryl ester was obtained as a white solid in 25% yield. $^1$H NMR (CD$_3$OD, δ): 7.06–7.28 (m, 10 H, Ar), 2.65 (t, 2 H, J$_{P,H}$=21.4 Hz, P—CH$_2$—P); $^{31}$P NMR (CD$_3$OD, δ): 15.41 (s). Equiv. Wt.: calc. 164.1 g/mol, found 167.0 g/mol. M.P. 181–183° C. (lit. 177–179° C.). [Lang et al., *Anorg. Allg. Chem.*, 536:187–196(1986)]

Methylenebis(1H, 1H-heptafluoro-n-butyl methyl phosphonate), (C$_3$F$_7$CH$_2$)$_2$Me$_2$[MBP]: This mixed fluoroalkyl ester was obtained as a colorless oil in 25% yield after purification by flash chromatography (40:60 v/v ethyl acetate/CH$_2$Cl$_2$). $^1$H NMR (CDCl$_3$, δ): 4.62 (m, 4 H, OCH$_2$), 3.85 & 3.82 (d, 6 H, J$_{P,H}$=12.0 Hz, OCH$_3$), 2.62 & 2.61 (t, 2 H, J$_{P,H}$=21.6 Hz, P—CH$_2$—P); $^{31}$P N (CDCl$_3$, δ): 21.75 & 21.57 (s). Anal. calc. for C$_{11}$H$_{12}$O$_6$P$_2$: C, 23.26; H, 2.13, found: C, 23.14; H, 2.30.

EXAMPLE 3

Preparations Via Scheme 3

These tetraesters are prepared by the 1H-tetrazole catalyzed esterification of methylenebis-(phosphonic dichloride) using a procedure similar to that described above for the synthesis of the P,P'-dialkyl-P,P'-dimethyl methylenebisphosphonates. In the preparation of the homoleptic methylenebis-phosphonate tetraesters, R$_4$[MBP], the reaction was carried in a single step using four equivalents of the alcohol, as is seen Scheme 3. The homoleptic tetraester formed in this step subsequently can be hydrolyzed to the symmetric partial ester using a variety of dealkylating reagents.

Homoleptic tetraesters of methylenebis-phosphonic acid were generally prepared following this procedure using 2-ethyl-1-hexanol, 1-butanol, 1-hexanol, cyclohexanol, phenol, 1H, 1H-heptafluoro-1-butanol and 3-trimethylsilyl-1-propanol. The yield of anhydrous tetraester obtained after purification using this procedure was generally very high; i.e., 85–95%. Reagents that can be used to selectively hydrolyze methylenebisphosphonates to the partial esters include trimethylsilyl halides, mineral acids, lithium halides and secondary amines, as discussed before.

General Procedure to Homoleptic Tetraesters of Methylenebisphosphonic Acid

Methylenebis(phosphonic dichloride) (1.00 g 4.00 mmol) and 1H-tetrazole (0.05 g 0.7 mmol) were placed in a 100 mL Schlenk flask and dissolved in 50 mL of benzene while vigorously stirring under a nitrogen atmosphere. When the dissolution was complete, a solution of the alcohol (16.0 mmol) and diisopropylethylamine (1.53 mL, 17.6 mmol) in 20 mL of benzene was added drop-wise through an addition funnel over a 2 hour period. After stirring the reaction overnight (about 16–18 hours) at room temperature under a nitrogen atmosphere, the solvent was removed in vacuo, the resulting residue dissolved in hexane and the diisopropylammonium and tetrazonium salts were removed by filtration using a Hirsch funnel. The solution was concentrated in vacuo and the resulting crude product, a light yellow oil, was purified by flash chromatography (10:90 v/v acetone/hexane; first band).

The hydrolysis of EH$_4$[MBP] using trimethylsilyl bromide (TMSBr) was investigated for a very restricted set of reaction conditions. The dealkylation of EH$_4$ [MBP] using 3 equivalents of TMSBr at room temperature for 48 hours, as described above for the Me$_2$EH$_2$[MBP] deprotection, resulted in a crude product containing several methylenebisphosphonic acid partial esters, indicating that the reaction was not selective under these conditions. This product is suitable for use as technical grade Dipex®. It is likely that the desired selectivity can be achieved using shorter reaction times and stoichiometric amounts of the TMSBr deprotecting reagent.

Characterization of Compounds Prepared via Scheme 3

Methylenebis(di-n-butyl phosphonate), Bu$_4$[MBP]: This tetraester was obtained as a colorless oil in 98% yield. $^1$H NMR (CDCl$_3$, δ): 4.10 (dt, 8 H, J$_{P,H}$=J=6.7 Hz, OCH$_2$), 2.44 (t, 2 H, J$_{P,H}$=21.0 Hz, P—CH$_2$—P), 1.67 (p, 8 H, J=6.8 Hz, OCH$_2$CH$_2$), 1.41 (m, 8 H, CH$_2$CH$_3$), 0.93 (t, 12 H, J=7.2 Hz, CH$_3$); $^{31}$P NMR (CDCl$_3$, δ): 19.74 (s).

Methylenebis(di-n-hexyl phosphonate), H$_4$[MBP]: This tetraester was obtained as a colorless oil in 85% yield. $^1$H NMR (CDCl$_3$, δ): 4.09 (dt, 8 H, J$_{P,H}$=J=6.9 Hz, OCH$_2$), 2.45 (t, 2 H, J$_{P,H}$=21.0 Hz, P—CH$_2$—P), 1.68 (p, 8 H, J=6.9 Hz, OCH$_2$CH$_2$), 1.20–1.41 (m, 24 H, CH$_2$), 0.89 (t, 12 H, J=7.0 Hz, CH$_3$); $^{31}$P NMR (CDCl$_3$, δ): 19.71 (s).

Methylenebis(dicyclohexyl phosphonate) half-hydrate, cH$_4$[MBP]×½ H$_2$O: This compound was obtained as a colorless oil in 85% yield after purification by flash chromatography (25:75 v/v acetone/hexane; R$_f$=0.9). $^1$H NMR (CDCl$_3$, δ): 4.47 (m, 4 H, OCH), 2.41 (t, 2 H, J$_{P,H}$=21.0 Hz, P—$CH_2$—P), 1.15–2.08 (m, 40 H, $CH_2$); $^{31}$P NMR ($CDCl_3$, δ): 17.72 (s). Anal. calc. for $C_{25}H_{47}O_{6½}P_2$: C, 58.47; H, 9.23, found: C, 58.72; H, 9.43.

Methylenebis(di-2-ethylhexyl phosphonate) ($EH_4$[MBP]): This compound was obtained as a colorless oil in 85% yield after purification by flash chromatography (10:90 v/v acetone/hexane; $R_f$=0.85, first band). $^1$H NMR ($CDCl_3$, δ): 4.00 (m, 8 H, $OCH_2$), 2.44 (t, 2 H, $J_{P,H}$=21.2 Hz, P—$CH_2$—P), 1.58 (m, 4 H, CH), 1.22–1.49 (m, 32 H, $CH_2$), 0.89 (t, 24 H, J=7.6 Hz, $CH_3$); $^{31}$P NMR ($CDCl_3$, δ): 19.86 (s). Anal. calc. for $C_{33}H_{70}O_6P_2$: C, 63.43; H, 11.29, found: C, 63.41; H, 11.51. HRMS-FAB (m/z): [M+H]$^+$ calc. 625.4727, found 625.4702.

Methylenebis(di-3-(trimethylsilyl)propyl phosphonate), $TMSP_4$[MBP]: This ester was obtained as a colorless oil in 83% yield after purification by flash chromatography (50:50 v/v diethyl ether/ethyl acetate; $R_f$=0.8). $^1$H NMR ($CDCl_3$, δ): 4.04 (dt, 8 H, $J_{P,H}$=J=7.2 Hz, $OCH_2$), 2.45 (t, 2 H, $J_{P,H}$=21.0 Hz, P—$CH_2$—P), 1.67 (m, 8 H, $OCH_2CH_2$), 0.49 (m, 8 H, $CH_2Si$), 0.0 (s, 36 H, $Si(CH_3)_3$); $^{31}$P NMR ($CDCl_3$, δ): 19.99 (s). Anal. calc. for $C_{25}H_{62}O_6P_2Si_4$: C, 47.43; H, 9.87, found: C, 47.11; H, 9.85. HRMS-FAB (m/z): [M+H]$^+$ calc. 633.3178, found 633.3164.

Methylenebis(diphenyl phosphonate), $Ph_4$[MBP]: This tetraaryl ester was obtained as a white solid in 85% yield after recrystallization from diethyl ether. $^1$H NMR ($CDCl_3$, δ): 7.20–7.40 (m, 20 H, Ar), 3.12 (t, 2H, $J_{P,H}$=21.0 Hz, P—$CH_2$—P); $^{31}$P NMR ($CDCl_3$, δ): 10.74 (s). M.P. 81–83° C. (lit. 82–83° C.). [Lang et al., *Anorg. Allg. Chem.*, 536:187–196(1986)]

Methylenebis(di-1H,1H-heptafluoro-n-butyl phosphonate) (($C_3F_7CH_2$)$_4$[MBP]): This fluoroalkyl tetraester was obtained as a yellow oil in 82% yield after purification by flash chromatography (50:50 v/v diethyl ether/ethyl acetate; $R_f$=0.85). $^1$H NMR ($CDCl_3$, δ): 4.61 (m, 8 H, $OCH_2$), 2.84 (t, 2 H, $J_{P,H}$=22.0 Hz, P—$CH_2$—P); $^{31}$P NMR ($CDCl_3$, δ): 21.32 (s) Anal. calc. for $C_{17}H_{10}F_{28}O_6P_2$: C, 22.58; H, 1.11, found: C, 22.25; H, 1.10.

EXAMPLE 4

Results with Various Catalysts

A variety of aromatic cyclic nitrogen bases have been investigated as potential catalysts for the synthesis of symmetric alkylenebisphosphonate esters from the acid chloride. The compounds investigated are structurally similar to the nitrogen heterocycle catalysts typically used for acyl chloride esterification. [Haslam, *Tetrahedron*, 36:2409–2434 (1980).] The ring size as well as the number and position of nitrogen atoms in the ring was varied systematically in an effort to determine the effect of these structural modifications on catalyst selectivity.

The procedure followed was identical to that described for the synthesis of DIPEX® extractant by Scheme 1 with 10 mg of the indicated aromatic cyclic nitrogen base replacing the 1 H-tetrazole. The nitrogen heterocycles studied were pyridine, 4-(dimethylamino)pyridine, imidazole, 1-methylimidazole, 1-acetylimidazole, histamine dihydrochloride, 1H-1,2,3-triazole and 1H-tetrazole.

All of the compounds investigated catalyze the reaction, however, not all are selective, see Table 1, hereinafter. The best catalysts, 1H-tetrazole and 1H-1,2,3-triazole, were found to provide both high yields and very high selectivity. Introducing 1H-tetrazole as a 0.45 M solution in acetonitrile (commercially available from Fluka, Milwaukee, Wis.) was as effective as adding the catalyst as a neat solid.

Another compound that provided very high yields and is nearly as selective as these two aromatic bases is 1-methylimidazole. The DIPEX® extractant product prepared using 1-methylimidazole or imidazole to catalyze the esterification of methylenebis(phosphonic dichloride) with two equivalents of 2-ethylhexanol contains a very small amount of the triester; i.e., levels just detectable by $^1$H NMR spectroscopy.

Pyridine is somewhat less selective than these two catalysts. In the case of pyridine, a small amount of the triester is observed in the isolated product by $^1$H and $^{31}$P NMR spectroscopy. However, the product obtained with all three compounds is useful, because the presence of a small amount of a triester is not expected to affect the performance of the product as an extractant.

Histamine dihydrochloride and 1-acetylimidazole were less selective than 1-methylimidazole. The use of these bases as catalysts further complicated the esterification by the formation of small amounts of other side products; i.e., phosphonamides and acyl compounds, respectively.

The C-substituted aromatic base 4-(dimethylamino) pyridine, DMAP, provided poor selectivity and relatively low yield of a product that contained a significant amount of the triester present in the isolated oil. Presumably, the nucleophilicity of the pyridine nitrogen is too greatly enhanced by resonance delocalization of the amine nitrogen lone pair onto the ring and the selectivity of the catalyst is lost.

Based on the data in Table 1, it appears that ring size alone is not a determining factor in controlling catalyst selectivity. Aromatic nitrogen bases with two or more nitrogen atoms in the ring appear to be the preferred catalysts for coupling an alkylenebis(phosphonic dichloride) with an alcohol, as these compounds provided the greatest selectivity for producing the symmetric P,P'-disubstituted partial ester product.

The $pK_b$ values for the catalysts that provided the best selectivity are greater than 7.0. Aromatic nitrogen bases that contain an atom with a lone electron pair adjacent to the nucleophilic center as exemplified by 1H-tetrazole and 1H-1,2,3-triazole are the preferred catalysts. If there is an atom containing one or more unshared electron pairs adjacent to the attacking atom on a nucleophile, the nucleophilicity of the attacking atom appears to be enhanced. [J. March, *Advanced Organic Chemistry: Reactions, Mechanisms and Structure*, 4$^{th}$ ed., John Wiley & Sons, NY (1992) pp. 351–352.]

TABLE 1

Catalyzed Coupling of Methylenebis(phosphonic dichloride) with Two Equivalents of 2-Ethylhexanol

| Catalyst | Structure | Yield (%) | pKa | pKb |
|---|---|---|---|---|
| Imidazole | 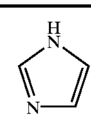 | 90.5* | 6.99[2] | 7.01 |
| 4-(Dimethylamino)pyridine | | 89.2[a] | 9.7[3] | 4.3 |

TABLE 1-continued

Catalyzed Coupling of Methylenebis(phosphonic dichloride) with Two Equivalents of 2-Ethylhexanol

| Catalyst | Structure | Yield (%) | pKa | pKb |
|---|---|---|---|---|
| Histamine dihydrochloride | 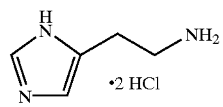 | 83.3* | 6.04[2] 9.75[2] | 7.96, 4.25 |
| 1-Methyl-imidazole | 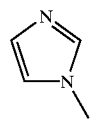 | 97.3* | 6.95[2] | 7.05 |
| 1H-1,2,3-Triazole | 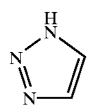 | 88.2 | 1.17[2] | 12.82 |
| 1H-Tetrazole | 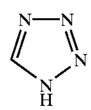 | 97.3[b] | 4.87[1] | 9.13 |
| 1-Acetyl-imidazole | 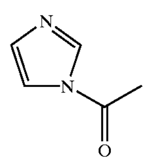 | 92.5* | 3.6[4] | 10.4 |
| Pyridine | 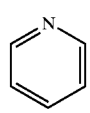 | 96.1* | 5.23[2] | 8.77 |

*Small amount of a triester present in the isolated product (1–3%).
[a]Catalyst lacks selectivity. A significant amount of a triester (~30%) is present in the isolated product.
[b]1H-tetrazole added as the commercially available 0.45 M solution in acetonitrile is as selective as the solid sample.
[1]Kortum et al., Dissociation Constants of Organic Acids in Aqueous Solution, International Union of Pure and Applied Chemistry, Butterworths, London (1961) p. 531.
[2]CRC Handbook of Chemistry and Physics, 3rd Electronic Edition, CRC Press LLC (2001) @www.crcpress.com.
[3]Hierl, et. al., J. Amer. Chem. Soc., 101: 6020–6022 (1979).
[4]CRC Handbook of Biochemistry, 2nd ed., Sober et al eds., The Chemical Rubber Co., Cleveland OH (1970) pp. 209–220.

Each of the patents, applications and articles cited herein is incorporated by reference. The use of the article "a" or "an" is intended to include one or more.

From the foregoing, it will be observed that numerous modifications and variations can be effectuated without departing from the true spirit and scope of the novel concepts of the present invention. It is to be understood that no limitation with respect to the specific examples presented is intended or should be inferred. The disclosure is intended to cover by the appended claims all such modifications as fall within the scope of the claims.

What is claimed is:

1. A process for preparing a P,P'-ester of a $C_1$–$C_{10}$ alkylenebisphosphonic acid that comprises the steps of:
   (a) admixing one mole of $C_1$–$C_{10}$ alkylenebis(phosphonic dichloride) with about two moles of an alcohol having a molecular weight of about 250 or less in the presence of a catalytic amount of an alpha-effect cyclic aromatic amine and at least two moles of a base in an aprotic solvent to form a first reaction mixture;
   (b) maintaining said first reaction mixture for a time period sufficient to form a $C_1$–$C_{10}$ alkylenebis(chloro ester phosphonate) and a reaction mixture depleted of said alcohol;
   (c) admixing said formed $C_1$–$C_{10}$ alkylenebis(chloro ester phosphonate) with an excess of a hydroxylated compound, YOH, that can be water, the same or different alcohol having a molecular weight of about 250 or less, or a primary $C_1$–$C_8$ alcohol to form a second reaction mixture; and
   (d) maintaining said second reaction mixture for a time period sufficient to form a $C_1$–$C_{10}$ alkylenebis(ester phosphonate) that is the corresponding partial ester, homoleptic tetraester or mixed tetraester, respectively.

2. The process according to claim 1 wherein said alcohol having a molecular weight of about 250 or less is a (tri-$C_1$–$C_4$ alkyl)silyl $C_3$–$C_8$ alkyl alcohol, a polyfluorinated alcohol, a $C_4$–$C_{10}$ alkyl or cycloalkyl alcohol or a phenyl ring-containing alcohol having six to ten carbon atoms.

3. The process according to claim 1 wherein said base is a tertiary amine.

4. The process according to claim 1 wherein said one mole of $C_1$–$C_{10}$ alkylenebis(phosphonic dichioride) is admixed with slightly less than two moles of said alcohol.

5. The process according to claim 1 wherein said aprotic solvent is an aromatic solvent.

6. The process according to claim 1 wherein said alcohol and base are added to the acid chloride.

7. The process according to claim 6 wherein said alcohol and base are admixed prior to being added to the acid chloride.

8. The process according to claim 1 wherein said $C_1$–$C_{10}$ alkylene group is a methylene or ethylene group.

9. The process according to claim 1 wherein said $C_1$–$C_{10}$ alkylenebis(ester phosphonate) is the corresponding partial ester.

10. The process according to claim 9 including the further step of recovering said partial ester.

11. The process according to claim 1 wherein YOH is the same alcohol that is reacted under basic conditions to form a $C_1$–$C_{10}$ alkylenebis(ester phosphonate) that is the homoleptic tetraester.

12. The process according to claim 11 including the further step of recovering said homoleptic tetraester.

13. The process according to claim 12 including the further step of selectively hydrolyzing the recovered homoleptic tetraester to form the partial ester.

14. The process according to claim 13 including the further step of recovering said partial ester.

15. The process according to claim 1 wherein YOH is a different alcohol having a molecular weight of about 250 or less that is reacted under basic conditions to form a $C_1$–$C_{10}$ alkylenebis(ester phosphonate) that is the mixed tetraester.

16. The process according to claim 15 including the further step of recovering said mixed tetraester.

17. The process according to claim 16 including the further step of selectively hydrolyzing the recovered mixed tetraescer to form the partial ester.

18. The process according to claim 17 including the further step of recovering said partial ester.

19. The process according to claim 1 wherein said alpha-effect cyclic aromatic amine is 1H-1, 2,3-triazole or 1H-tetrazole.

20. A process for preparing a P,P'-diester of a methylenebisphosphonic acid that comprises the steps of:
    (a) admixing one mole of methylenebis-(phosphonic dichioride) with slightly less than two moles of an alcohol having a molecular weight of about 250 or less in the presence of a catalytic amount of an alpha-effect cyclic aromatic amine and at least two moles cf a tertiary amine base in an aromatic solvent to form a first reaction mixture, said alcohol and base being admixed with each other prior to being added to the acid chloride;

(b) maintaining said first reaction mixture for a time period sufficient to form a P,P'-diester of methylenebis-sphosphonic acid chloride and a reaction mixture depleted of said alcohol;

(c) admixing said formed P,P'-diester of methylenebi-sphosphonic acid chloride with an excess of water to form a second reaction mixture; and (d) maintaining said second reaction mixture for a time period sufficient to form a P,P'-diester of a methylenebis(phosphonic acid).

21. The process according to claim 20 wherein said base is selected from the group consisting of triisopropylamine, triethylamine, diisopropylethylamine, tripropylamine, tributylamine, quinuclidine, 1,8-bis(dimethylamino) naphthalene, pyridine, 1H-1,2,3-triazole and 1H-tetrazole.

22. The process according to claim 20 wherein said alcohol having a molecular weight of about 250 or less is a $C_4$–$C_{10}$ alkyl or cycloalkyl alcohol, a (tri-$C_1$–$C_4$ alkyl)silyl $C_3$–$C_8$ alkyl alcohol, a polyfluorinated alcohol, and a phenyl ring-containing alcohols having six to ten carbon atoms.

23. The process according to claim 22 wherein said alcohol is a $C_4$–$C_{10}$ alkyl or cycloalkyl alcohol that is selected from the group consisting of n-butanol, sec-butanol, iso-butyl alcohol, amyl alcohol, sec-amyl alcohol, 3-pentanol, iso-amyl alcohol, tert-amyl alcohol, neo-pentyl alcohol, cyclohexanol, 3-methylcyclohexanol, hexanol, 2-methyl-1-pentanol, 4-methyl-2-pentanol, 2-ethyl-1-butanol, 1-octanol, 2-ethyl-1-hexanol, 2,4,4-trimethylpentanol and decanol.

24. The process according to claim 22 wherein said alcohol is a (tri-$C_1$–$C_4$ alkyl)silyl $C_3$–$C_8$ alkyl alcohol that is selected from the group consisting of 3-(trimethylsilyl)-1-propanol, 4-(trimethylsilyl)-1-butanol and 8-(trimethylsilyl)-1-octanol.

25. The process according to claim 22 wherein said alcohol is a polyfluorinated alcohols that is selected from the group consisting of 1H,1H-heptafluoro-1-butanol, 1,1,2,2,3,3,4,4-octafluouro-1-pentanol,1H,1H-pentafluoro-1-propanol, 2,2,3,3-tetrafluoro-1-propanol, 3-(perfluorohexyl)-1-propanol and 2H-hexafluoro-2-propanol.

26. The process according to claim 22 wherein said alcohol is a phenyl ring-containing alcohol having six to ten carbon atoms that is a phenol or an aralkyl alcohol.

27. The process according to claim 20 including the further step of recovering said P,P'-diester of a methylenebi-sphosphonic acid.

28. The process according to claim 20 wherein said alpha-effect aromatic amine contains 5 or 6 members in the ring and has a $pK_b$ value in excess of about 7.

29. A process for preparing a P,P'-di-$C_4$–$C_{10}$ alkyl or cycloalkyl methylenebisphosphonic acid that comprises the steps of:

(a) admixing oine mole of methylenebis-(phosphonic dichiorid) with slightly less than two moles of a $C_4$–$C_{10}$ alkyl or cycloalkyl alcohol in the presence of a catalytic amount of an alpha-effect aromatic amine containing 5 or 6 members in the ring that has a $pK_b$ value in excess of about 7 and at least two moles of a tertiary amine base in an aromatic solvent to form a first reaction mixture, said alcohol and base being admixed with each other prior to being added to the acid chloride;

(b) maintaining said first reaction mixture for a time period sufficient to form a methylenebis-(chloro $C_4$–$C_{10}$ alkyl or cycloalkyl ester phosphonate) and a reaction mixture depleted of said $C_4$–$C_{10}$ alkyl or cycloalkyl alcohol;

(c) admixing said formed methylenebis-(chloro $C_4$–$C_{10}$ alkyl or cycloalkyl ester phosphonate) under basic conditions with an excess of a $C_1$–$C_8$ alkyl alcohol to form a second reaction mixture;

(d) maintaining said second reaction mixture for a time period sufficient to form a methylenebis($C_4$–$C_{10}$ alkyl or cycloalkyl $C_1$–$C_8$ alkyl ester phosphonate);

(e) recovering the mixed tetraester so formed; and (f) selectively hydrolyzing the recovered mixed tetraester to form the P,P'-di-$C_4$–$C_{10}$ alkyl or cycloalkyl methyl-enebisphosphonic acid.

30. The process according to claim 29 wherein said base is selected from the group consisting of triisopropylamine, triethylamine, diisopropylethylamine, tripropylamine, tributylamine, quinuclidine, 1,8-bis(dimethylamino) naphthalene, pyridine, 1H-1,2,3-triazole and 1H-tetrazole.

31. The process according to claim 29 wherein said $C_4$–$C_{10}$ alkyl or cycloalkyl alcohol is selected from the group consisting of include n-butanol, sec-butanol, iso-butyl alcohol, amyl alcohol, sec-amyl alcohol, 3-pentanol, iso-amyl alcohol, tert-amyl alcohol, neo-pentyl alcohol, cyclohexanol, 3-methylcyclohexanol, hexanol, 2-methyl-1-pentanol, 4-methyl-2-pentanol, 2-ethyl-1-butanol, 1-octanol, 2-ethyl-1-hexanol, 2,4,4-trimethylpentanol and decanol.

32. The process according to claim 29 including the further step of recovering said P,P'-di-$C_4$–$C_{10}$ alkyl or cycloalkyl methylenebisphosphonic acid.

33. The process according to claim 29 wherein said alpha-effect cyclic aromatic amine has a $pK_b$ value in excess of about 8.

34. A process for preparing a homoleptic tetraester methylenebisphosphonate that comprises the steps of:

(a) admixing one mole of methylenebis-(phosphonic dichioride) with about four moles of an alcohol having a molecular weight of about 250 or less in the presence of a catalytic amount of an alpha-effect cyclic aromatic amine and at least four moles of a tertiary amine base in an aromatic solvent to form a first reaction mixture, said alcohol and base being admixed with each other prior to being added to the acid chloride; and (b) maintaining said first reaction mixture for a time period sufficient to form a homoleptic tetraester methylenebisphosphonate and a reaction mixture depleted of said alcohol.

35. The process according to claim 34 wherein said base is selected from the group consisting of triisopropylamine, triethylamine, diisopropylethylamine, tripropylamine, tributylamine, quinuclidine, 1,8-bis(dimethylamino) naphthalene, pyridine, 1H-1,2,3-triazole and 1H-tetrazole.

36. The process according to claim 34 wherein said alcohol having a molecular weight of about 250 or less is a $C_4$–$C_{10}$ alkyl or cycloalkyl alcohol, a (tri-$C_1$–$C_4$ alkyl)silyl $C_3$–$C_8$ alkyl alcohol, a polyfluorinated alcohol, or a phenyl ring-containing alcohols having six to ten carbon atoms.

37. The process according to claim 34 wherein said alcohol is a $C_4$–$C_{10}$ alkyl or cycloalkyl alcohol that is selected from the group consisting of n-butanol, sec-butanol, iso-butyl alcohol, amyl alcohol, sec-amyl alcohol, 3-pentanol, iso-amyl alcohol, tert-amyl alcohol, neo-pentyl alcohol, cyclohexanol, 3-methylcyclohexanol, hexanol, 2-methyl-1-pentanol, 4-methyl-2-pentanol, 2-ethyl-1-butanol, 1-octanol, 2-ethyl-1-hexanol, 2,4,4-trimethylpentanol and decanol.

38. The process according to claim 34 wherein said alcohol is a (tri-$C_1$–$C_4$ alkyl)silyl $C_3$–$C_8$ alkyl alcohol that is selected from the group consisting of 3-(trimethylsilyl)-1-propanol, 4-(trimethylsilyl)-1-butanol and 8-(trimethylsilyl)-1-octanol.

39. The process according to claim 34 wherein said alcohol is a polyfluorinated alcohol that is selected from the group consisting of 1H,1H-heptafluoro-1butanol, 1,1,2,2,3,3,4,4-octafluoro-1-pentanol, 1H,1H-pentafluoro-1-propanol, 2,2,3,3-tetrafluoro-1-propanol, 3-(perfluorohexyl)-1-propanol and 2H-hexafluoro-2-propanol.

40. The process according to claim 34 wherein said alcohol is a phenyl ring-containing alcohol having six to ten carbon atoms that is a phenol or an aralkyl alcohol.

41. The process according to claim 34 including the further step (c) of recovering the homoleptic tetraester so formed.

42. A process for the preparation of a P,P'-diester of methylenebisphosphonic acid that comprises the steps of forming the homoleptic methylenebis (ester phosphonate) acid according to claim 34 and including the further step (d) of selectively hydrolyzing the recovered homoleptic tetraester to form the P,P'-diester of methylenebisphosphonic acid.

43. The process according to claim 34 wherein said cyclic aromatic amine is a alpha-effect cyclic aromatic amine containing an atom with a lone electron pair adjacent to the nucleophilic center.

44. The process according to claim 43 wherein said cyclic alpha-effect aromatic amine has 5 or 6 members in the ring and has a $pK_b$ value in excess of about 7.

45. A process for preparing a P,P'-di-$C_4$–$C_{10}$ alkyl or cycloalkyl methylenebisphosphonic acid that comprises the steps of:

(a) admixing one mole of methylenebis-(phosphonic dichloride) with four moles of a $C_4$–$C_{10}$ alkyl or cycloalkyl alcohol in the presence of a catalytic amount of an alpha-effect cyclic aromatic amine and at least four moles of a tertiary amine base in an aromatic solvent to form a reaction mixture, said alcohol and base being admixed with each other prior to being added to the acid chloride;

(b) maintaining said reaction mixture for a time period sufficient to form a homoleptic methylenebis($C_4$–$C_{10}$ alkyl or cycloalkyl ester phosphonate) and a reaction mixture depleted of said $C_4$–$C_{10}$ alkyl or cycloalkyl alcohol;

(c) recoverinq the homoleptic tetraester so formed; and (d) selectively hydrolyzing the recovered homoleptic tetraester to form the P,P'-di-$C_4$–$C_{10}$ alkyl or cycloalkyl methylenebisphosphonic acid.

46. The process according to claim 45 wherein said base is selected from the group consisting of triisopropylamine, triethylamine, diisopropylethylamine, tripropylamine, tributylamine, quinuclidine, 1,8-bis(dimethylamino) naphthalene, pyridine, 1H-1,2,3-triazole and 1H-tetrazole.

47. The process according to claim 45 wherein said $C_4$–$C_{10}$ alkyl or cycloalkyl alcohol is selected from the group consisting of include n-butanol, sec-butanol, iso-butyl alcohol, amyl alcohol, sec-amyl alcohol, 3-pentanol, iso-amyl alcohol, tert-amyl alcohol, neo-pentyl alcohol, cyclohexanol, 3-methylcyclohexanol, hexanol, 2-methyl-1-pentanol, 4-methyl-2-pentanol, 2-ethyl-1-butanol, 1-octanol, 2-ethyl-1-hexanol, 2,4,4-trimethylpentanol and decanol.

48. The process according to claim 45 including the further step of recovering said P,P'-di-$C_4$–$C_{10}$ alkyl or cycloalkyl methylenebisphosphonic acid.

49. The process according to claim 45 wherein said hydrolysis is carried out using hydrochloric acid or trimethylsilyl bromide.

* * * * *